US008659391B2

(12) United States Patent
Pradeep et al.

(10) Patent No.: US 8,659,391 B2
(45) Date of Patent: Feb. 25, 2014

(54) MULTIELEMENT AND MULTIPROPERTY TAGGING

(75) Inventors: Thalappil Pradeep, Chennai (IN); Panikkanvalappil Ravindranathan Sajanlal, Chennai (IN)

(73) Assignee: Indian Institute of Technology Madras, Chennai (IN)

( * ) Notice: Subject to any disclaimer, the term of this patent is extended or adjusted under 35 U.S.C. 154(b) by 750 days.

(21) Appl. No.: 12/636,370

(22) Filed: Dec. 11, 2009

(65) Prior Publication Data
US 2011/0043331 A1   Feb. 24, 2011

(30) Foreign Application Priority Data

Aug. 18, 2009   (IN) .......................... 1967/CHE/2009

(51) Int. Cl.
G05B 19/00   (2006.01)
(52) U.S. Cl.
USPC .............. 340/5.86; 252/587; 283/72; 283/74; 162/140; 977/902; 382/181; 382/190
(58) Field of Classification Search
USPC .................... 340/5.86; 252/587; 283/72–114; 162/140; 977/902–962
See application file for complete search history.

(56) References Cited

U.S. PATENT DOCUMENTS

| | | | |
|---|---|---|---|
| 4,183,989 A | 1/1980 | Tooth | |
| 4,446,204 A | 5/1984 | Kaule et al. | |
| 5,713,485 A * | 2/1998 | Liff et al. | 221/2 |
| 5,853,464 A | 12/1998 | Macpherson et al. | |
| 6,234,537 B1 * | 5/2001 | Gutmann et al. | 283/86 |
| 6,255,948 B1 | 7/2001 | Wolpert et al. | |
| 6,515,749 B2 | 2/2003 | Pipino | |
| 6,610,351 B2 | 8/2003 | Shchegolikhin et al. | |
| 6,686,074 B2 | 2/2004 | Muth et al. | |
| 6,692,030 B1 | 2/2004 | Phillips | |
| 6,764,970 B1 | 7/2004 | Kuoni | |
| 6,859,309 B2 * | 2/2005 | Fischer et al. | 359/359 |
| 7,288,320 B2 | 10/2007 | Steenblik et al. | |
| 7,628,887 B2 * | 12/2009 | Jaaskelainen et al. | 162/140 |
| 8,069,782 B2 * | 12/2011 | Fragala et al. | 101/28 |
| 8,253,536 B2 * | 8/2012 | Kaminska et al. | 340/5.86 |

(Continued)

FOREIGN PATENT DOCUMENTS

| | | |
|---|---|---|
| JP | 2006-247871 A | 9/2006 |
| WO | 2006086008 A2 | 8/2006 |
| WO | WO-2007/031077 | 3/2007 |
| WO | 2007149120 A2 | 12/2007 |
| WO | 2008010822 A2 | 1/2008 |
| WO | 2008030219 A2 | 3/2008 |

OTHER PUBLICATIONS

International Preliminary Report on Patentability for PCT/IB2010/002006 DTD Feb. 21, 2012.
Sajanial P. R. et al., "Mesoflowers: A new class of highly efficient surface-enhanced Raman active and infrared absorbing materials", Tsinghua University Press, co-published with Springer-Verlag GmbH, Chemical and Materials Science, Nano Research, vol. 2, No. 4,pp. 306-320, DOI 10.1007/s12274-009-9028-5, Apr. 17, 2009.
J. Fang et al, "Gold Mesostructures with Tailored Surface Topography and Their Self-Assembly Arrays for Surface-Enhanced Raman Spectroscopy," NanoLetters, 10 (12), pp. 5006-5013, Nov. 19, 2010, retrieved from https://pubs.acs.org/doi/abs/10.1021/nl1012085.

(Continued)

Primary Examiner — Brian Zimmerman
Assistant Examiner — Ryan Sherwin
(74) Attorney, Agent, or Firm — Foley & Lardner LLP

(57) ABSTRACT

An embodiment relates to a man-made object comprising a distinctive structure with a feature to identify the object, wherein the object has a size such that the object is observable under visible light, wherein the feature is embedded in or on the object and a size of the feature is such that the feature is not observable under visible light, wherein the feature comprises an attribute originating from the feature, and wherein the attribute defines the feature.

21 Claims, 16 Drawing Sheets

(56) References Cited

U.S. PATENT DOCUMENTS

| | | |
|---|---|---|
| 2002/0021003 A1 | 2/2002 | McGrew |
| 2005/0277710 A1 | 12/2005 | Joyce et al. |
| 2007/0112784 A1 | 5/2007 | Blumenau |
| 2008/0179405 A1 | 7/2008 | Benderly |
| 2009/0008925 A1* | 1/2009 | Blondiaux et al. .............. 283/85 |
| 2009/0220789 A1 | 9/2009 | Desimone et al. |
| 2010/0195916 A1 | 8/2010 | Blondiaux et al. |
| 2010/0284917 A1 | 11/2010 | Kustner et al. |
| 2011/0049239 A1 | 3/2011 | Kukushkin et al. |

OTHER PUBLICATIONS

"Fluorescence Detection of Counterfeit US Currency," JASCO, Inc. Molecular Spectroscopy, Feb. 2004, p. 26.

http://microtracesolutions.com/ (retrieved Apr. 29, 2013).

International Search Report for International Application No. PCT/IB2010/002006, European Patent Office, The Hague, Netherlands, mailed on Feb. 4, 2011.

Leech, P. W. And Zeidler, H., "Microrelief structures for anti-counterfeiting applications," Microelectronic Engineering, vol. 65, Issue 4, pp. 439-446 (2003).

\* cited by examiner (a)

(b)

(a)

(b)

(c)

MULTIELEMENT AND MULTIPROPERTY TAGGING

CROSS-REFERENCE TO RELATED APPLICATIONS

The present application claims the benefit of Indian Patent Application No. 1967/CHE/2009, filed Aug. 18, 2009, which is hereby incorporated by reference in its entirety.

TECHNICAL FIELD

The embodiments relate to the field of tagging, more particularly tagging using an object having features embedded in or on the object.

BACKGROUND

Counterfeiting and piracy are major threats faced by nations across the world, both politically and economically. Several approaches have been suggested to solve this problem. For example, WO/2006/086008 discloses nanoparticles as covert taggants in currency, bank notes, and related documents; U.S. Pat. No. 6,692,030 discloses security document with nano-patterns; WO/2008/010822 discloses authenticating and identifying objects using nanoparticles; (WO/2008/030219) discloses remote identification of explosives and other harmful materials; U.S. Pat. No. 6,515,749 discloses sensitive and selective chemical sensor with nanostructured surfaces; (WO/2007/149120) discloses arrays of nano structures for surface-enhanced Raman scattering; U.S. Pat. No. 6,610,351 discloses Raman-active taggants and their recognition; U.S. Pat. No. 5,853,464 discloses pigment compositions; Spectroscopy, Feb. 26, 2004, discloses fluorescence detection of counterfeit US currency; and Microelectron. Eng., 2003, 65, 439, discloses microrelief structures for anti-counterfeiting applications.

SUMMARY

The embodiments herein relate to a man-made object comprising a distinctive structure with a feature to identify the object, wherein the object has a size such that the object could be observable under visible light, wherein the feature could be embedded in or on the object and a size of the feature could be such that the feature could be not observable under visible light, wherein the feature comprises an attribute originating from the feature, and wherein the attribute defines the feature.

Preferably, one of the dimensions of the object could be in a range of 0.1 to 10 μm and the size of the feature could be about 100 nm or less.

Preferably, the feature comprises a plurality of unique elements, each unique element having a distinct pattern.

Preferably, the feature comprises a plurality of unique elements, each unique element having a distinct property.

Preferably, the feature comprises a tag, the tag being associated with the object such that the identification of the tag allows authentication of the object.

Preferably, the tag could be selected from the group consisting of a molecular tag, a biological tag, an optical tag, an electronic tag, a magnetic tag, a fluorescent tag, a Raman spectroscopy tag, an electron microscopy tag, an X-ray microcopy tag, and combinations thereof.

Preferably, the feature could be not observable without a specialized device configured to detect the feature.

Preferably, the specialized device could be configured to detect optical, Raman, fluorescence, electron, X-ray or magnetic properties of the feature.

Preferably, the feature comprises an unique element at molecular, atomic or single particle levels.

Preferably, the feature comprises a plurality of unique elements that are configured to be detected at different stages of authentication of the object.

Preferably, the feature comprises a plurality of unique elements, each unique element having a distinct pattern and a distinct property.

Preferably, the feature has specific structural attributes.

Preferably, the feature comprises a tag, the tag being associated with the object such that the identification of the tag allows authentication of the object.

Another embodiment relates to a system comprising multiple diagnostic devices configured to authenticate an object comprising a feature to identify the object, wherein the feature comprises a plurality of unique elements, each unique element having a distinct pattern and a distinct property.

Preferably, the multiple diagnostic devices comprise an optical diagnostic device, a Raman diagnostic device, an electron diagnostic device, an X-ray diagnostic device, a magnetic diagnostic device or combinations thereof.

Another embodiment relates to a method comprising characterizing a feature embedded in or on an object and authenticating the object based on a result of characterizing the feature, wherein the feature comprises a plurality of unique elements that are configured to be detected at different stages of authenticating the object.

Preferably, the characterization could be done by a system comprising multiple diagnostic devices.

Preferably, the multiple diagnostic devices comprise an optical diagnostic device, a Raman diagnostic device, an electron diagnostic device, an X-ray diagnostic device, a magnetic diagnostic device or combinations thereof.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
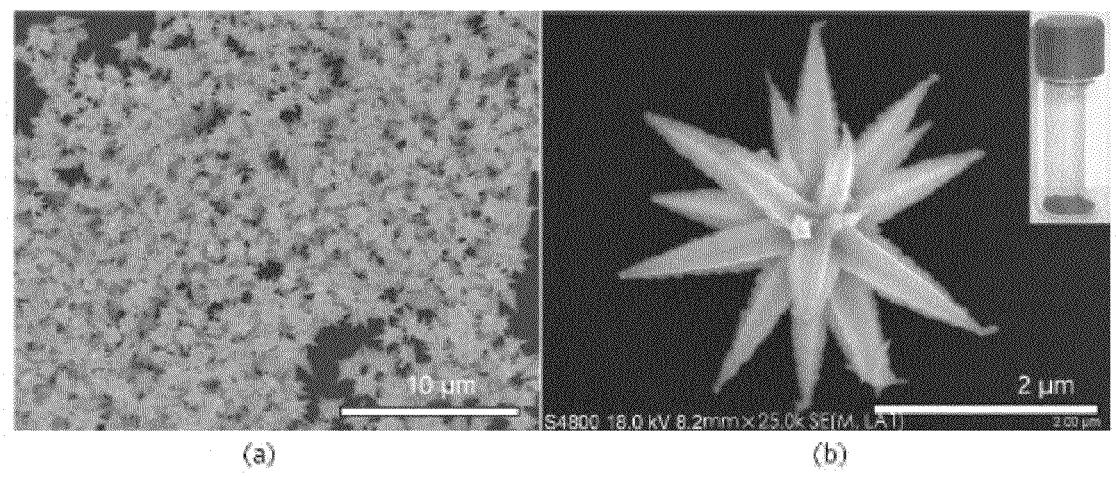
FIG. 1(a) shows a large area FESEM image of gold mesoflowers anchored on a conducting glass substrate; (b) FESEM image of a gold mesoflower. The inset shows a photograph of the mesoflower powder.

An embodiment disclosed herein relates to an object having embedded features such that the object could be used as detection tag and detected by a combined optical, Raman, fluorescence, electron, X-ray microscopy and/or magnetic detection based approach to provide fool-proof security to something to which the object is part of, using unique structures with nanoscale features. Such a detection technique allows imaging using some or all the above mentioned techniques to be done simultaneously or sequentially, at a single particle level. While the presence of unique structural features of the object are observable with visible light, and could be used to authenticate the object at home or elsewhere, the embedded structures and molecular features are observed by sophisticated equipment.

An object refers to a man-made object having a distinctive structure with a feature to identify the object, wherein the object has a size such that the object could be observable under visible light. The distinctive structure could be a mesoscale structure (mesostructure) or a nano-scale structure (nanostructure). The feature could be embedded in or on the object and has a size such that the feature could be not observable under visible light. The feature has an attribute (an inherent characteristic) originating from the object. The attribute could be a signature that defines the feature, which in turn could define the distinctive structure and/or the object.

Detection at a single particle level refers to the ability to detect a single object, e.g., a single "mesoflower" particle, having a distinctive structure with a feature with multielement and multiproperty attributes that can hold lots of unique information which cannot be duplicated easily. Analysis of such a single mesoflower could be sufficient for the authentication of an object on which the feature could be embedded. The mesoflower could be unsymmetrical at the single particle level resembling several natural objects and made up of a large number of stems with unusual pentagonal symmetry. The mesostructured material could have a high degree of structural purity with star-shaped, nano-structured stems. The mesoflower could be obtained in high yield, without any contaminating structures and its size could be tuned from nano- to meso-dimensions.

An embodiment herein relates to fool-proof security detection of a product having an object using combined optical, Raman, fluorescence, electron, X-ray, and/or magnetic diagnostics. For example, the embodiment could relate to a molecular detection protocol with an unusual and unique micron scale object, possessing nanoscale features, such as a mesoflower, which could be used for generating security features for currencies and other documents. The embodiment could comprise a highly surface-enhanced Raman spectroscopy (SERS) or fluorescence-active metal mesoflower on which a Raman or fluorescent-active molecule, having an easily distinguishable Raman or fluorescent spectrum, could be adsorbed or attached on a product that has to be authenticated.

The authentication method could be implemented at various levels of identification involving an array of microscopic and spectroscopic tools as the mesostructure such as a mesoflower can be imaged using optical, Raman, and fluorescence microscope, scanning electron microscope (SEM) and energy dispersive analysis of X-rays (EDAX). A micron scale object with unique structural features could be observed under an optical microscope, while the specific nanoscale features could be seen under electron and X-ray microscopes. The feature could include molecular tags that could be detected using Raman or fluorescent spectroscopes. Raman microscopy could also reveal the molecular distribution on the mesostructure. The elemental mapping of the mesostructure can also be done using EDAX. The spatial distributions of molecules/atoms along the entire structure of the substrate and a multitude of molecular tags, with specific Raman or fluorescence features, which can be synthesized, provide multilayer security for such systems. One or more of the above said instrumentation techniques can be used simultaneously for a given application, depending on the level of security needed.

The shape of the object of the embodiments herein could be as unique as a fingerprint or a biological object such as a starfish or a flower, which cannot be replicated in its entirety at the atomic level. The uniqueness of a single mesoflower particle comes about in view of: (1) the unique shape as in the case of a star fish, aloe vera, pineapple, etc., (2) unique molecular markers having well-defined molecular features in Raman, fluorescence and infrared spectroscopy, (3) elemental features due to the embedded metals such as gold, silver, platinum, etc. and (4) nanoscale features of the structure which could be arising due to the synthetic control. It would be impossible to duplicate all of them simultaneously. This implies that a single mesoflower particle with multielement and multiproperty attributes can hold lots of unique information which cannot be duplicated easily. Analysis of such a single mesoflower, which could be referred to as a single particle, could be sufficient for the authentication of an object on which the mesoflower is embedded.

The ability to authenticate an object could be based at least in part on the creation of unique mesoscale (of length in the range of 0.1-10 μm) objects with embedded nanoscale features and specific structural attributes.

While the object as a whole could be observable to the end user with the help of simple microscopes, the enhanced detection of molecular features due to the nanostructure allows unique spectroscopic, microscopic, and magnetic characterization using sophisticated instruments. Several of the unique features can also be ascertained by simple devices available to the common man.

The feature that one produces through the techniques disclosed herein could be as unique as a fingerprint or a biological object such as a starfish or a flower, which cannot be replicated in its entirety right from mesoscale and nanoscale up to the atomic level.

The different levels of security reading (optical, Raman, fluorescence, electron and/or X-ray microscopy) may be implemented at different stages of authentication in automated facilities. The method of providing security includes making specific nanoscale objects of well-defined shape, incorporating organic molecules of molecular tags having distinct Raman/fluorescence/infrared features on the nanostructures, embedding the materials on the substrate at predetermined locations in specific patterns or otherwise so as to create a hidden security coding. The features could be read by fast spectrometers. Using a sensitive Raman spectrometer, the embedded Raman features of the incorporated tag molecules can be analyzed easily within seconds. Since it could be a machine based detection technique, it could be possible to do the detection in an automated manner. Similarly, using suitable sophisticated instruments, the identification of the incorporated attributes on the mesoflowers can make automated. The different levels of security reading (optical, Raman, fluorescence, electron and X-ray microscopy) may be implemented at different stages of authentication in automated facilities. These may be installed at centralized locations for public awareness and information.

All the microscopic, spectroscopic, and magnetic attributes of the object cannot be duplicated at a single particle level. These attributes provide unprecedented multielemental and multiproperty tagging of security features to a product or an object for prevention of counterfeiting and authentication. The attributes could be inherent structural attributes that are unique to the mesoflowers.

The mesoflowers with high structural purity could be made by synthetic methodology. Each parameter in the synthesis produces a mesoflower with unique morphology. The uniqueness of the mesoflower comes about in view of: (1) the unique shape similar to aloe vera, pineapple, starfish, flower, etc. (2) unique molecular markers having well-defined molecular features in Raman and fluorescence spectrum, (3) elemental features due to the embedded metals such as gold, silver, platinum, etc. and (4) nanoscale patterning of the structure which could arise due to the synthetic control. It would be impossible to duplicate all of them simultaneously. The molecular markers could be read even when a few molecules are present due to the unique nanostructures present. There are virtually unlimited possibilities of Raman or fluorescent-active molecules, with unique spectroscopic features. Also, multiple molecules can be attached on mesoflowers. All of these attributes of a mesoflower are virtually impossible to duplicate.

The mesoflower could have unique morphology. Once it is embedded on a substrate such as paper documents, currencies, etc., it would not come out easily. The unique morphology enables the mesoflower to stick on a substrate firmly. For example, a counterfeited currency made by photocopying would not contain the mesoflower taggent. This can be checked easily by a simple hand held microscope. Incorporation of a surface-enhanced Raman scattering-active or fluorescent molecules tagged mesoflower into an object that has to be authenticated can provide multilevel security which would be difficult to counterfeit, while at the same time the mesoflower could be identified by using microscopic or spectroscopic techniques. The adsorbed Raman active molecules enable to collect unique Raman spectra and spectral image of the embedded mesoflower. Detailed investigation of the mesoflower using SEM or TEM could give the complicated geometry of the mesoflower that could be hard to replicate to provide another level of security. These are some examples for different levels of securities afforded by the embodiments herein.

The embodiments herein may be implemented at different stages of authentication. For example, the authentication technique could be a combined optical, Raman, electron and X-ray microscopy based approach to provide fool-proof security to a substrate using a unique mesoflower with nanoscale features. The different levels of securities as mentioned above may be implemented at different stages of authentication with mesoscale imaging being the first, followed by nanoscale imaging, which depending on the requirements in automated facilities and response times for such authentication can be as low as 10 millisecs.

For example, a surface-enhanced Raman spectroscopy (SERS) property of the mesoflower can be utilized as one of the levels of security. A Raman spectrometer can provide the unique spectral features of the adsorbed tag molecules. It would be possible to collect the Raman spectrum within few milliseconds depends on the instrumental capability. Such kind of spectrum would contain all the information about the tag molecules. Thus, it would be possible to authenticate an object using the Raman spectrometer within milliseconds.

The characterization of the mesoflower can be done by at least the following methods:
1. Visual detection of the embedded mesoflower using hand lens or optical microscope. (Here visual examination at a specific location in the object to be authenticated using hand lens would reveal the presence of complex-shaped particles).
2. Molecular spectral signatures from the adsorbed Raman or fluorescent specific molecules on the mesoflower surfaces using hand-held Raman or fluorescent spectrometer, respectively. A specific location in the object to be authenticated could be irradiated with laser or fluorescent source and resultant spectrum could be recorded. Then the spectrum could be matched with a library.
3. Molecular spectral signatures based imaging from the adsorbed Raman or fluorescent specific molecules using hand-held Raman or fluorescent spectrometer, respectively. A specific location in the currency could be scanned with a laser or fluorescent source and resultant Raman-based image could be recorded.
4. The fluorescent molecule on the mesoflower surface could be detected in presence of an ultraviolet light.

5. Analysis of unique morphology of the mesoflowers using scanning electron microscope.
6. Inspection of the morphology and finer atomic level details using transmission electron microscope.
7. Elemental composition analysis of the metal particles using energy dispersive X-rays analysis.

Preferably, all of the microscopic, spectroscopic, and magnetic attributes of a mesoflower cannot be duplicated at molecular, atomic, and single particle levels. A single mesoflower particle with multielement and multiproperty attributes can hold lots of unique information, all of which cannot be duplicated easily. Thus, analysis of such a single mesoflower could be generally sufficient for the authentication of an object on which the mesoflower would be embedded.

The embodiments herein provide unprecedented multielemental and multiproperty tagging of security features to a product or an object for prevention of counterfeiting and authentication. The embodiments provide multilevel security to an object, which has to be authenticated, by incorporating mesoflower-based security tags. Some or all of the mesoflowers on an object could be made of gold. It could be also possible to incorporate various metals onto the mesoflower by a simple synthetic protocol. Multielemental attributes can incorporated onto the mesoflower by this way. It could be also possible to incorporate Raman or fluorescent-active molecular tags, having an easily distinguishable Raman or fluorescent spectra to the synthesized mesoflower to form a highly SERS or fluorescent-active tagged metal mesoflower. These structural and compositional attributes and the adsorbed molecular markers present on the mesoflowers provide multielemental and multiproperty security to a product or an object for the prevention of counterfeiting.

The method of providing security comprises of making specific meso/nanoscale objects of well-defined shape, incorporating molecules/ions/species having distinct Raman, fluorescence, and infrared features on the nanostructures. In addition, elements such as Ag, Pt, Ni, Fe, Co, or any other suitable element, can be added to the earlier Au based mesoflower and the whole object can be incorporated on any substrate/object at predetermined locations in specific patterns or otherwise so as to create a hidden security coding. The entire mesostructure can be imparted magnetic properties as well.

Suitable instruments read/image/recognize specific characteristic features/information embedded on the mesoflower that could be available on an object. These features are read using the molecular, elemental, morphological and magnetic features exhibited by the materials used.

The shape and salient features thus obtained from this authenticating process, using instruments, distinguishes between real and fake objects. The different levels of security reading (optical, Raman, fluorescence, electron, X-ray, and magnetic properties) may be implemented at different stages of authentication in automated facilities.

The entire process can be automated which can authenticate objects from fake ones by using suitable image/pattern recognition system.

Examples

In one embodiment, the objects were gold mesoflowers. The mesoflowers resembled several natural objects made of a large number of stems with unusual pentagonal symmetry. These materials exhibit high degree of structural purity with star-shaped, nano-structured stems.

The mesoflower material was synthesized by following a seed-mediated growth procedure. The Au/oligoaniline seed nanoparticles were synthesized as per the disclosure in Sajanlal, P. R.; Sreeprasad, T. S.; Nair, A. S.; Pradeep, T. *Langmuir* 2008, 24, 4607. Besides oligo aniline as polymer, oligo- or poly-ortho, meta and para toludines or polymers of substituted anilines or oligomers or polymers of molecules such as ethylene, allene, vinylene, pyrole, pyridine, thiophene, or their substituted derivatives or other polymerizable molecules may also be used. Briefly, 50 mg of citric acid was dissolved in 75 mL of distilled water. The solution was maintained at 80° C. and 2 mL of 25 mM $HAuCl_4$ was added. After the color changes from pale yellow to pink, 200 µL distilled aniline was added followed by 1 mL of 25 mM $HAuCl_4$. Heating was continued for 5 more minutes. It is then allowed to cool to room temperature, centrifuged at 4000 rpm and the resultant light pink supernatant Au/oligoaniline nanoparticles were collected.

For making the gold mesoflower, a growth solution which contains 20 mL of cetyltrimethylammonium bromide, CTAB (100 mM), 335 µL of $Au^{3+}$ (25 mM), 125 µL of $AgNO_3$ (10 mM) and 135 µL of ascorbic acid (100 mM) was taken in a beaker. To this solution, 2 mL of the as prepared Au/oligoaniline nanoparticles were added. It was then kept at a temperature of 80 0 C for 1 h. The resultant solution was centrifuged at 4000 rpm for 5 min. The residue was redispersed in distilled water and again centrifuged for 5 min. Finally the solid residue was redispersed in distilled water, characterized and used for further experiments. This yielded mesoflowers of size 1-2 µm. In order to get mesoflowers of size ranging from 0.1-10 µm, the concentration and the amount of ingredients in the growth solution were varied into certain range such as 10-100 mL of CTAB (0.01-1.00 M), 100-1000 µL of $Au^{3+}$(10-100 mM), 125-500 µL of $AgNO_3$ (5-100 mM) and 100-1000 µL of ascorbic acid (10-1000 mM). The amount of seed particle added into this growth solution was also varied from 1 mL to 10 mL.

FIG. 1(a) shows the large area field emission scanning electron microscope (FESEM) image of a monolayer of gold mesoflowers anchored on an indium tin oxide (ITO) glass plate. FIG. 1(a) shows that the synthesis yields regular structures. In fact no spherical or other structures were found. All the mesoflowers showed the same morphology. The FESEM image in FIG. 1(b) of a single mesoflower reveals the highly complex anisotropic nature of the mesoflowers which are biomimetic structures, resembling aloe vera or pineapple. Each mesoflower is made up of a large number of spiky stems, which are projecting outward from the core, in all directions. From the FESEM images of the mesoflowers, it was found that the number of stems on each mesoflower varies from particle to particle. These stems make the mesoflowers three dimensional. The individual mesoflowers and all the particles observed were found to have more than 10 stems, ranging up to 20. A typical synthesis (using 20 mL growth solution, 3.3 mg $Au^{3+}$) made 2.9 mg of the material and a photograph of the mesoflower powder in the solid state is shown in the inset of FIG. 1(b).

Figure 2:
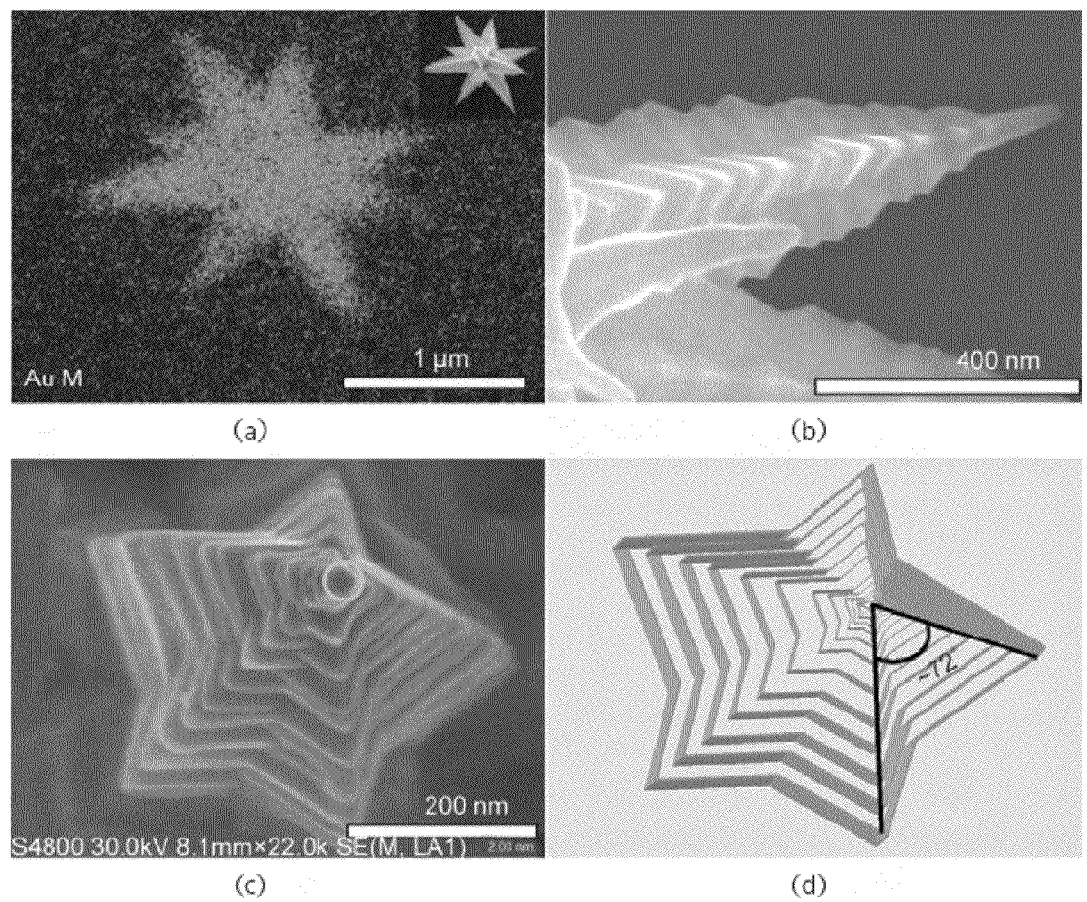
FIG. 2(a) shows an EDAX image using Au Mα taken from the mesoflower shown in the inset; (b) an enlarged FESEM image of a single stem of the mesoflower showing ridges along the edges; (c) top view of a single stem of the mesoflower showing the pentagonal structure and a nanoparticle on the apex (marked) and (d) a corresponding model.

In order to study the spatial distribution of gold in the mesoflower, elemental mapping of a single mesoflower was carried out using energy dispersive analysis of X-rays (EDAX). FIG. 2(a) shows an Au Mα-based image. From the EDAX analysis, it was confirmed that the mesoflower is almost completely made of gold. FIG. 2(b) shows a magnified SEM image of a single stem of the mesoflower. Each stem has ridges along its corners which give rise to a unique morphology. The presence of five edges gives a star-shaped appearance to the stem when it is viewed from the top and ridges along the corners of the stems give a stacked appearance. A view of the stem from its top appears as a star of edge length ~400 nm (FIG. 2(c)). A model of one such star-shaped stem is shown in FIG. 2(d).

Figure 3:
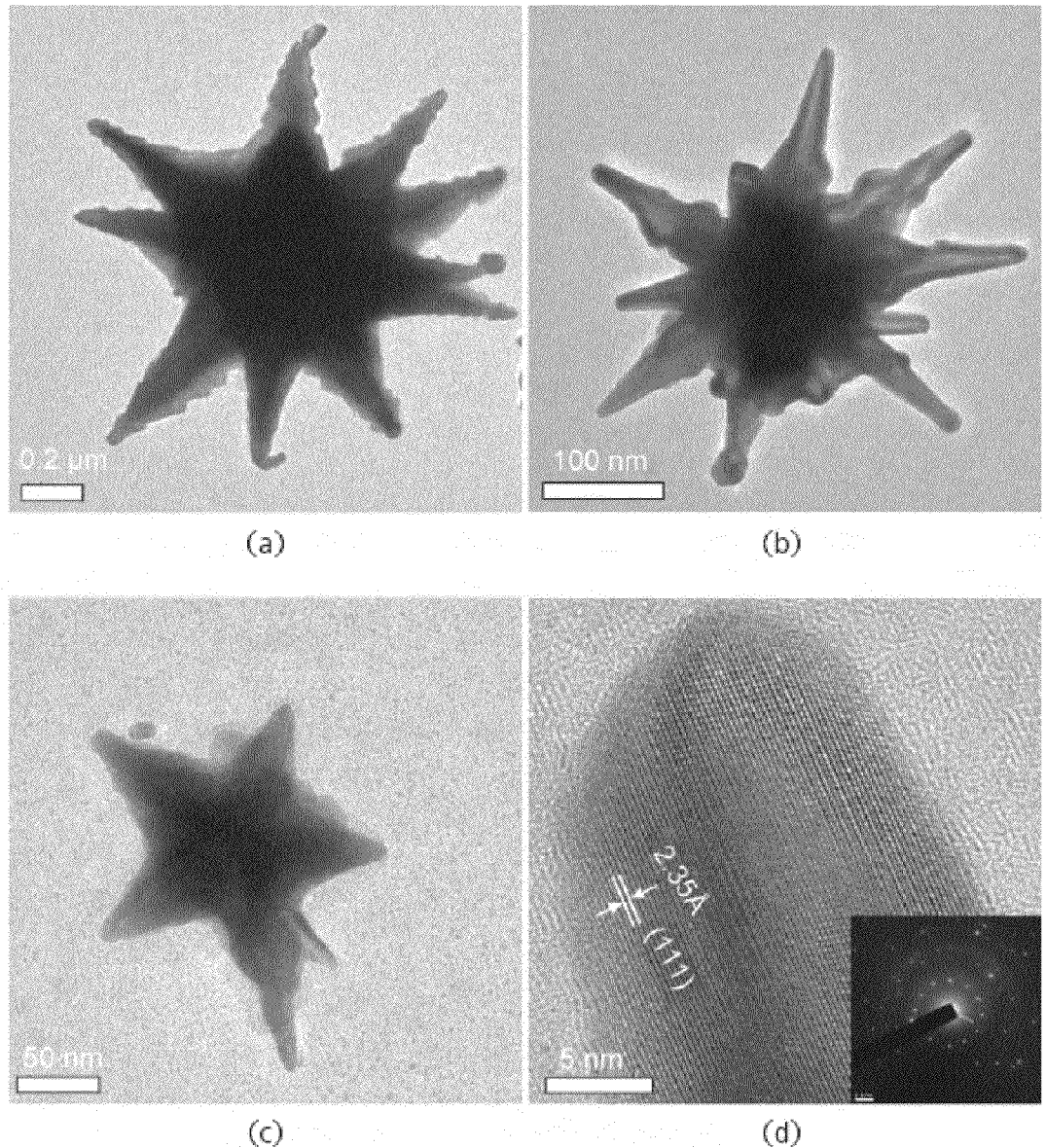
FIG. 3 shows TEM images of the mesoflowers of different sizes formed when varying amounts of seed solutions were added, such as (a) 2 mL, (b) 5 mL, and (c) 6 mL, into 20 mL of the growth solution; (d) a lattice-resolved TEM image taken from the tip of a mesoflower shown in (a); an SAED pattern taken from the tip of the mesoflower is shown in the inset of (d).

Furthermore, the size of the as synthesized three-dimensional mesoflowers can be controlled by altering the amount of the precursor Au/oligoaniline nanoparticles added. Mesoflowers larger than 1 μm in size were formed when 2 mL of the precursor nanoparticles were added to 20 mL of the growth solution under the optimized experimental conditions. FIG. 3(a) shows the transmission electron microscopy (TEM) image of such a single gold mesoflower. The average size of the mesoflowers was 1-2 μm. The size of the mesoflowers was found to decrease when the amount of seed solution added was increased to 5 mL, giving mesoflowers of length 0.5-1 μm (FIG. 3(b)). The size further decreased to ~150 nm by the addition of 6 mL of seed solution into the growth solution (FIG. 3(c)). This reveals the flexibility of our synthetic approach in tuning the size of the meso/nanoflowers. At higher seed concentrations, a large number of seed particles would take part in the growth process and the amount of gold ions in the growth solution would not be sufficient as they would be consumed before the complete growth of individual particles. A lattice-resolved TEM image of a stem of a mesoflower is shown in FIG. 3(d) and the corresponding selected area electron diffraction (SAED) is shown in the inset. The gold mesoflowers exhibit a lattice spacing of 2.35 Å, which corresponds to the (111) plane of gold. As TEM is a two dimensional projection, the three dimensionality of the object is not clear as in the SEM image.

Figure 4:
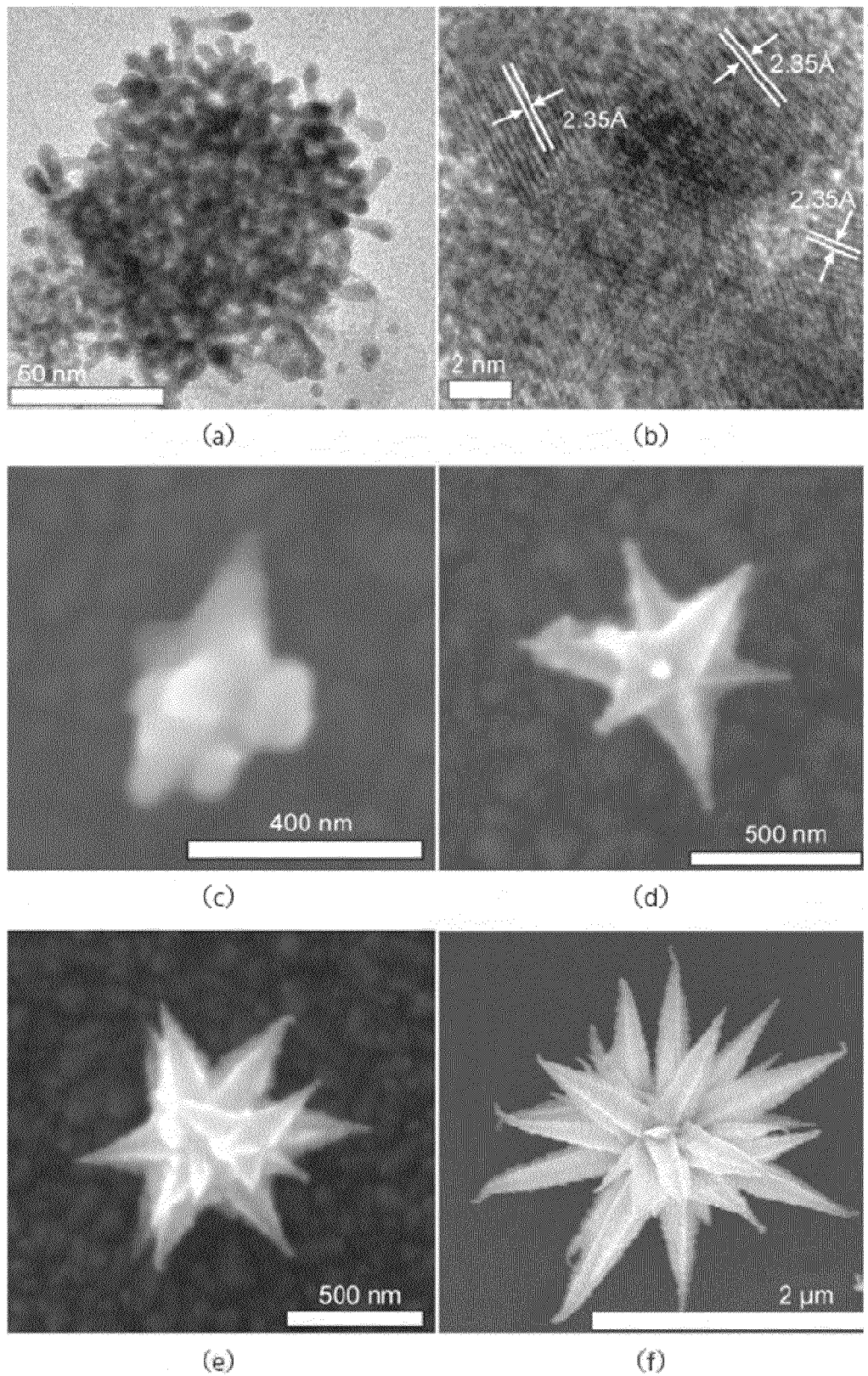
FIG. 4(a) shows TEM image of the Au/oligoaniline seed nanoparticle and (b) the lattice-resolved image taken from the seed particle; (c), (d), (e) and (f) are SEM images of the mesoflowers formed at various stages of growth 2, 5, 10, and 60 min, respectively.

The formation of mesoflowers depends on the morphology of the precursor Au/oligoaniline nanoparticles. FIG. 4(a) shows a TEM image of Au/oligoaniline seed nanoparticles. From the lattice-resolved image, it is clear that the smaller particles present inside the Au/oligoaniline seed are multitwinned. The gold (111) plane with d spacing of 2.35 Å is marked in the lattice-resolved image (FIG. 4(b)). FIG. 4(c) (f) show SEM images of the intermediate structures formed at different stages of the reaction. To collect the intermediate particles, the reaction was stopped after 2, 5, 10, and 60 min and the resultant solutions were centrifuged at 10,000 rpm in order to remove excess CTAB and other ions. The precipitate was washed with distilled water and analyzed using SEM. Within 5 min of the reaction, the seed particles formed the flower-like morphology in all its microscopic details, but they were smaller in size. The stems maintained their unusual pentagonal morphology. This indicates that the growth of the seed particles into the mesoflowers is very fast. Assembly of smaller structures such as nanoplates to form stems is unlikely on this time scale. Mesoflowers of size <500 nm were isolated after reaction for 5 min. This suggests that tuning the size of the mesoflowers as a function of time is possible. The star-shaped pyramids were formed by the selective and step-wise growth of the multitwinned seeds whose subsequent development leads to the formation of the five-edged stem, which gradually propagates resulting in a hierarchical pyramid of stars.

Figure 5:
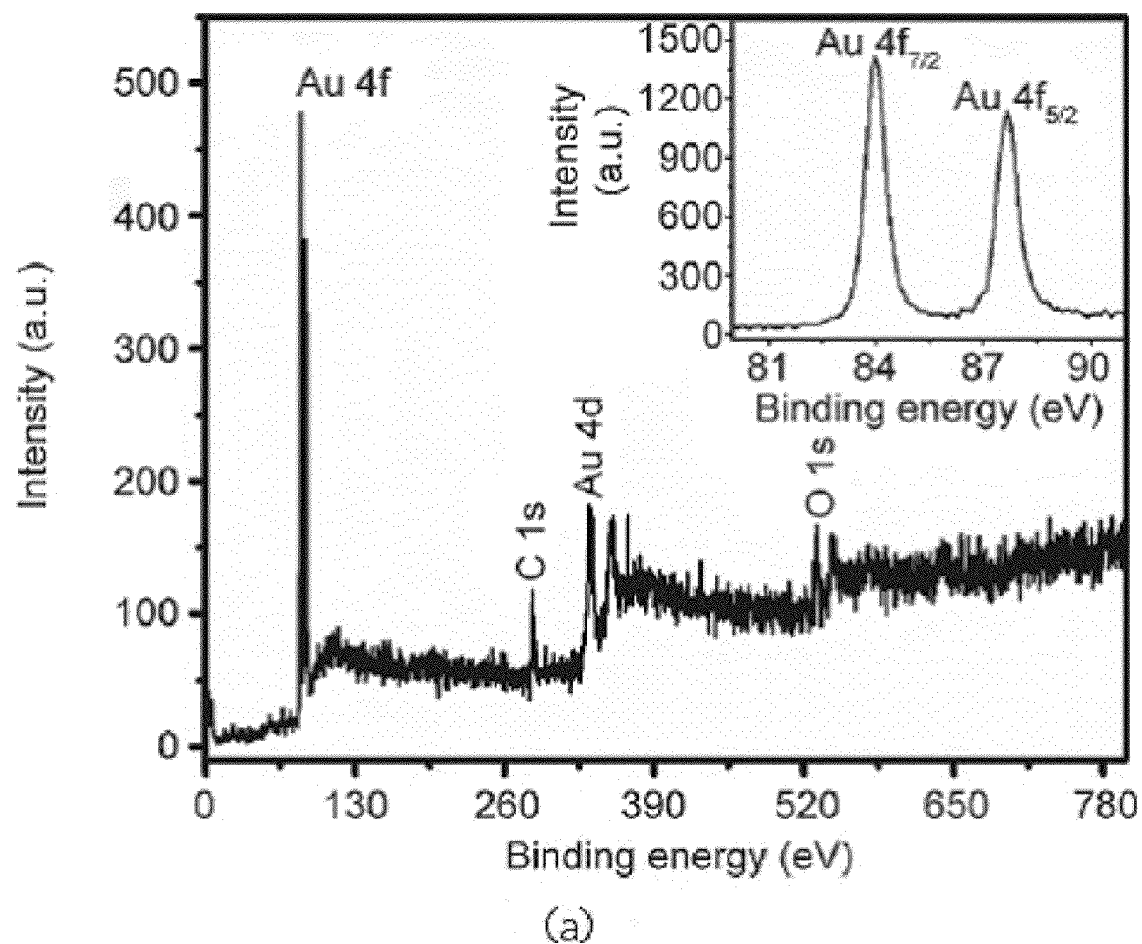
FIG. 5 shows XPS spectrum collected from (a) the gold mesoflower of size 1-2 μm and (b) Au/oligoaniline seed particles; the inset in (a) shows the enlarged spectrum in the Au 4f region.
Figure 5:
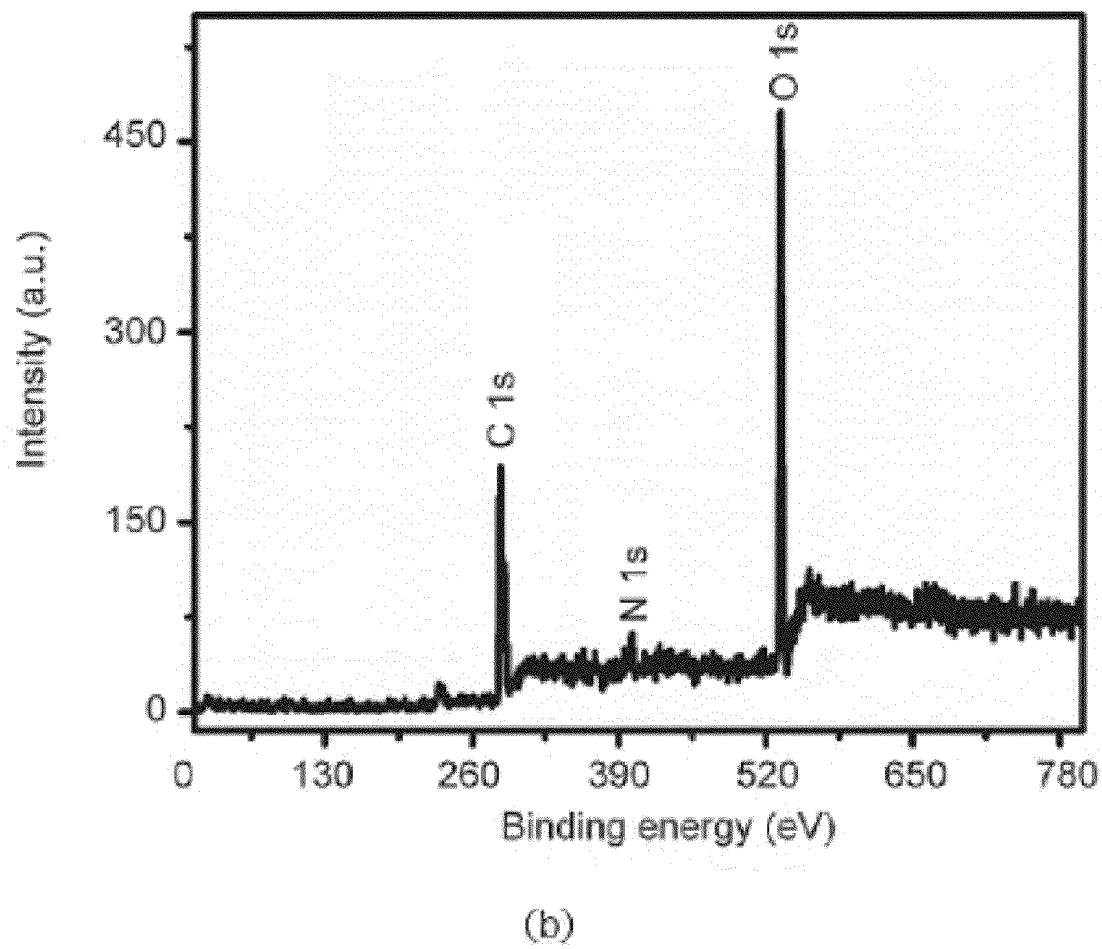

The elemental composition of the mesoflowers was studied using X-ray photoelectron spectroscopy (XPS). FIG. 5 shows a wide scan XPS spectrum of the mesoflowers and the parent Au/oligoaniline seed particles. The XPS spectrum of the mesoflower (FIG. 5(a)) revealed that it is composed of gold along with the expected surface contaminants. The prominent peaks seen are Au 4f, Au 4d, C s and O 1s. An enlarged XPS spectrum in the Au 4f region is shown in the inset of FIG. 6(a). The presence of Au $4f_{7/2}$ and Au $4f_{5/2}$ peaks, at ~83.9 and ~87.8 eV, respectively, confirms the existence of gold in its metallic form. The intensities of C 1s and O 1s are weak and can be attributed to the thin surfactant cover. CTAB is unlikely to be present at the detection level of XPS as no Br feature was detected (however, it is seen in mass spectrometry). In the case of Au/oligoaniline seed particles, the Au features in the XPS spectrum were masked by the high oligoaniline content (or due to the surface sensitivity of the technique) and the peaks due to the polymer were prominent (FIG. 5(b)). The presence of C 1s and N 1s suggests the existence of oligoaniline in the seed particles. The C 1s peak of Au/oligoaniline is split into three peaks in the binding energy range between 284 and 289 eV. The main peak at 284.5 eV is attributed to the C 1s of the oligoaniline originating from C—C and C—H bonds of the aromatic ring. The other two peaks situated at higher binding energy (286.5 and 288.8 eV) may be due to the C atoms directly attached to the N atom of the oligoaniline polymeric chain. Thus the observation of multiple peaks in the C 1s region confirms the presence of oligoaniline in the seed particle, although it is absent in the mesoflower. The oligoaniline is expected to be protonated under the acidic conditions employed and that is reflected in the N 1s binding energy (401.0 eV).

Figure 6:
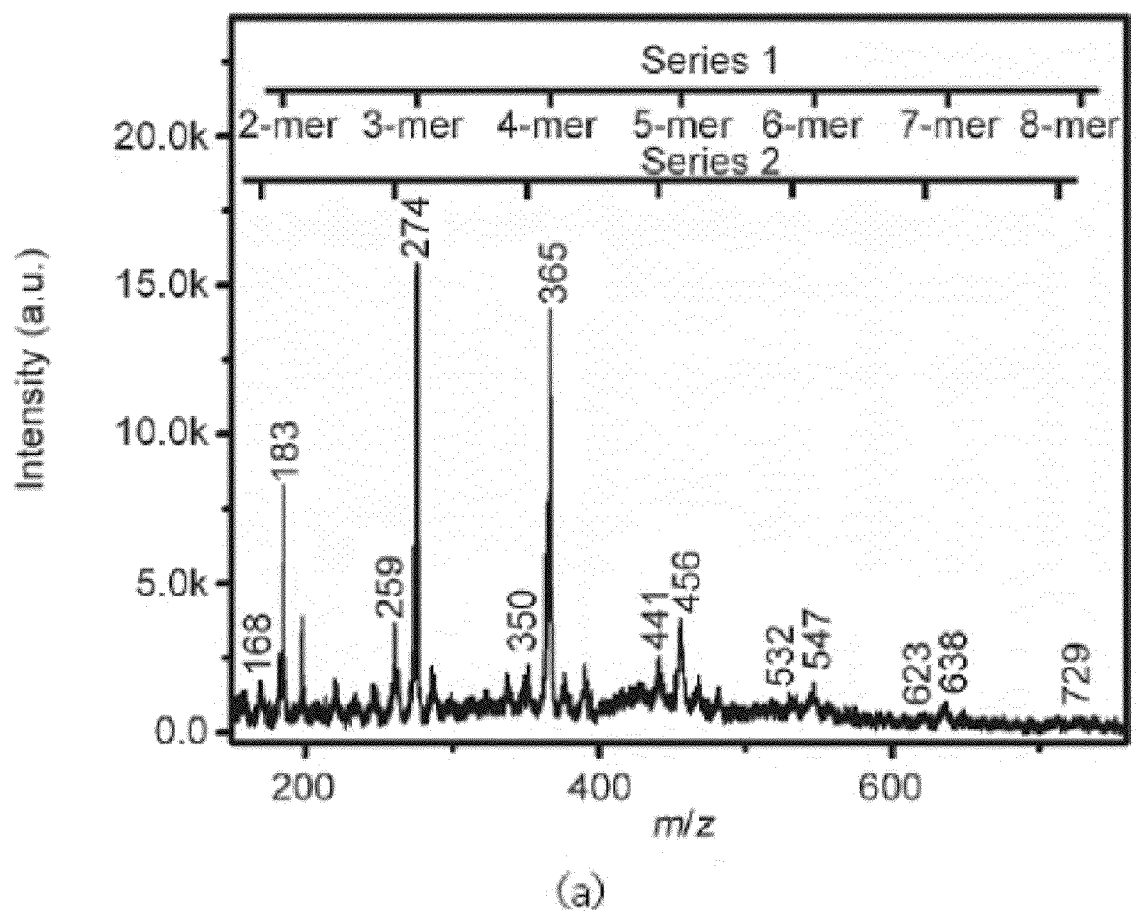
FIG. 6(a) shows LDI MS of the Au/oligoaniline seed taken in the positive mode. The two series of oligomeric peaks are indicated; peaks in series 2 occur at m/z 15 lower than the corresponding peaks in series 1; (b) and (c) are the LDI MS of the mesoflower taken in positive and negative modes, respectively. The peak at m/z 285 in (b) due to the cetyltrimethylammonium ion is enhanced due to its high sensitivity.
Figure 6:
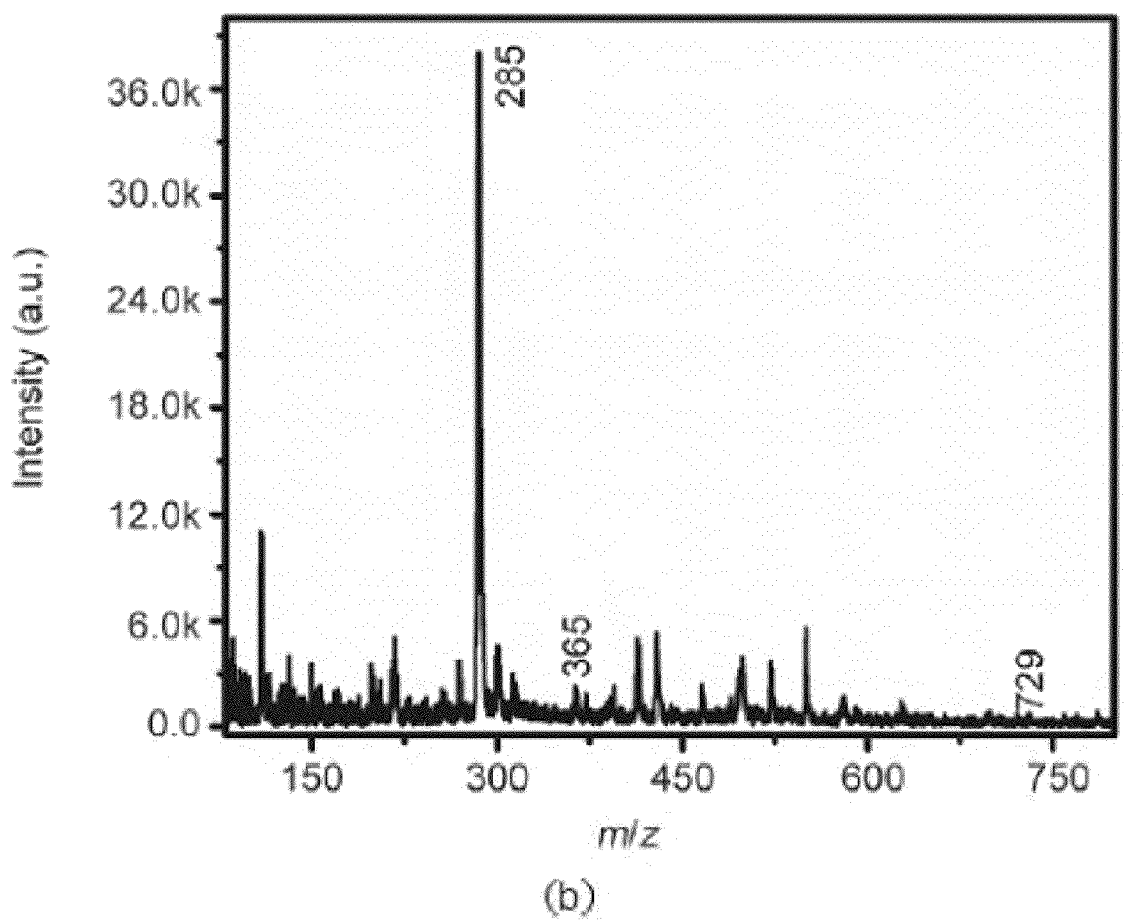
Figure 6:
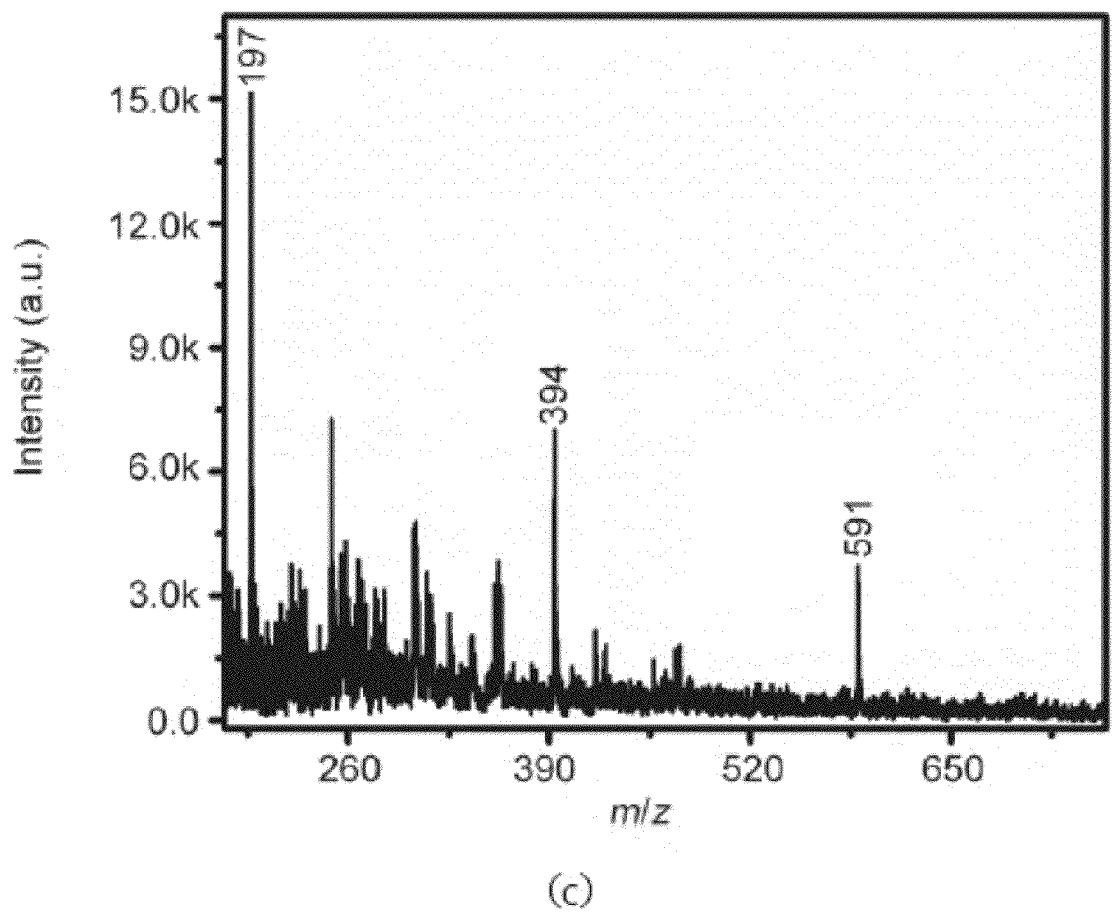

Laser desorption ionization mass spectra (LDI MS) of the Au/oligoaniline seed nanoparticles and mesoflowers are shown in FIG. 6. In the case of Au/oligoaniline seed particles, two series of peaks separated by m/z 91 were observed (FIG. 6(a)). This indicates the presence of oligoaniline. The peaks correspond to $(C_6H_4—NH)_n$, where n corresponds to 1 to 8. Corresponding peaks in the two series differ by m/z 15 (due to the loss of terminal amine, NH). In the case of the mesoflowers, although the CTAB concentration is low, it is the major peak (m/z 285) in the positive ion spectrum, as is typical of any quaternary ammonium ion-containing material (FIG. 6(b)). This is due to the high sensitivity of LDI for preformed ions. The very weak peaks appearing at m/z 365 and 729 may be due to the presence of trace amounts of oligoaniline (tetramer and octamer, respectively) adsorbed on the mesoflower even after washing. This clearly indicates that the oligoaniline is almost totally absent on the surface of the mesoflower, consistent with the XPS results. The peaks at m/z 197, 394, and 591 in the negative mode LDI MS (FIG. 6(c)) correspond to Au, Au$_2$, and Au$_3$ ions, typical of laser desorption of metallic gold.

Figure 7:
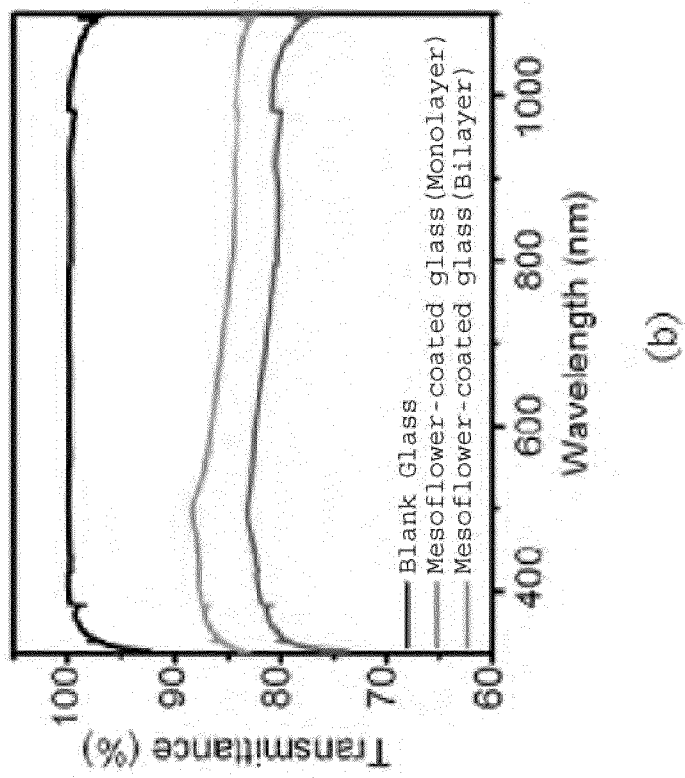
FIG. 7(a) shows UV-vis-NIR absorption spectra of monolayers of mesoflowers of various sizes and the corresponding spectrum of the blank glass substrate; (b) the transmittance spectra of the blank (black trace) as well as monolayer (green trace) and bilayer (red trace) of mesoflowers coated on the glass substrate; (c) photograph of the experimental set-up used for the real-time measurements of NIR-IR absorption properties of gold mesoflowers. The cardboard boxes are placed over a thermocol sheet. The thermocouple tip is at the centre of the box, as indicated in the picture. The thermocouple penetrates through the thermocol sheet. The whole set-up is kept on a table. Measurements were repeated with separate samples and on various days. (d) and (e) are plots of the variation of temperature inside the cardboard boxes as a function of exposure time for glass plates coated with a monolayer and bilayer of mesoflowers, respectively (the temperature fluctuations in (e) around 1500 s are due to the hindrance of the sunlight due to passing clouds). The initial increase in temperature, close to zero time, is very fast.
Figure 7:
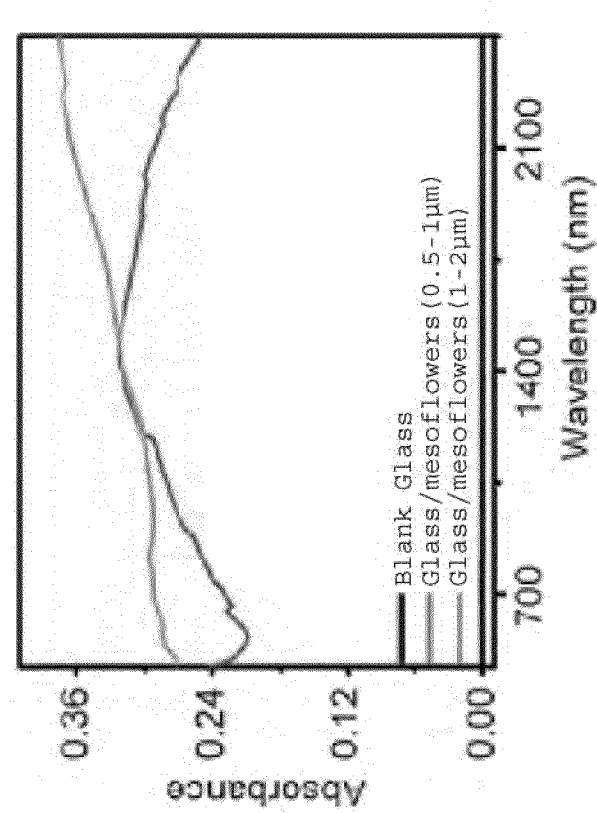
Figure 7:
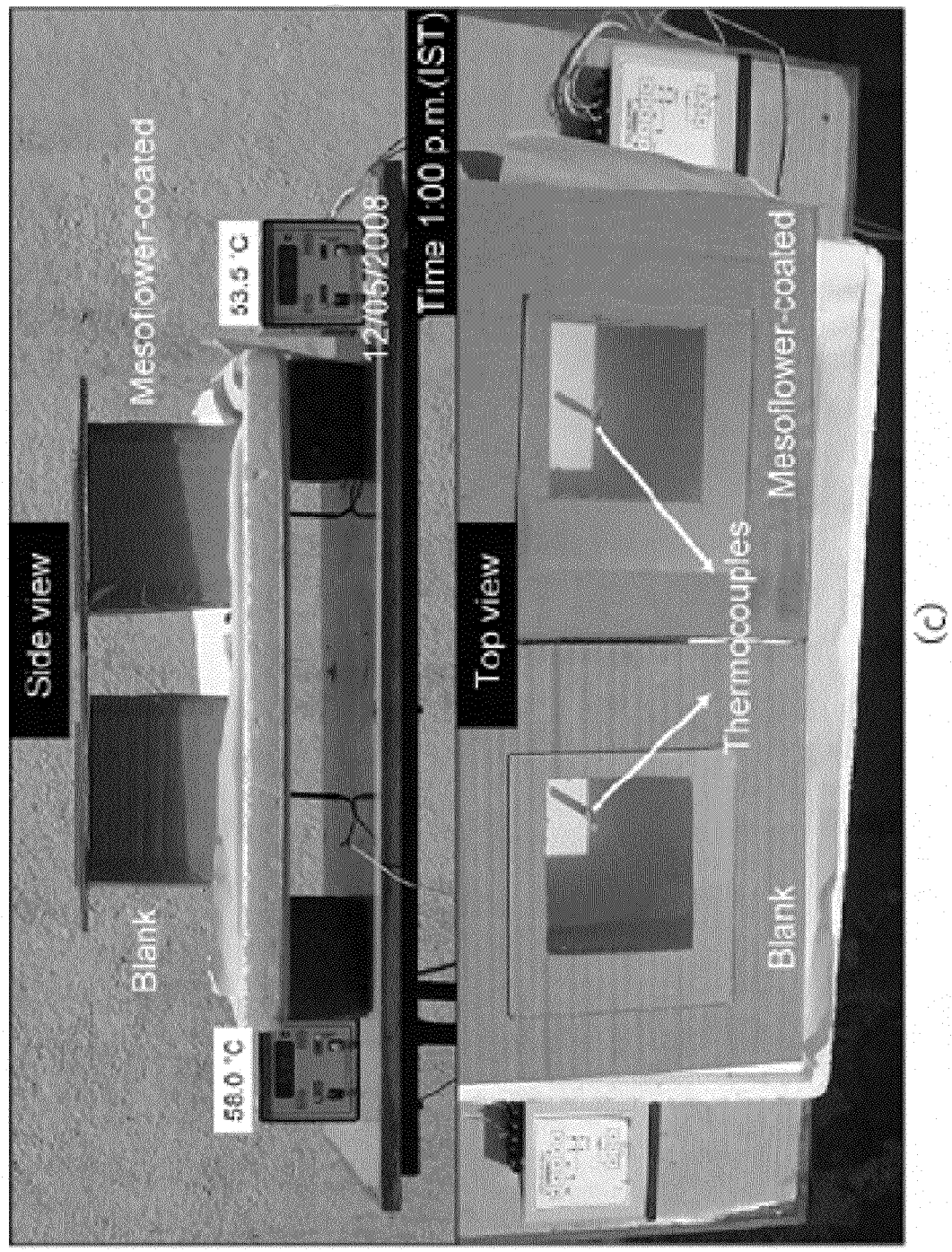
Figure 7:
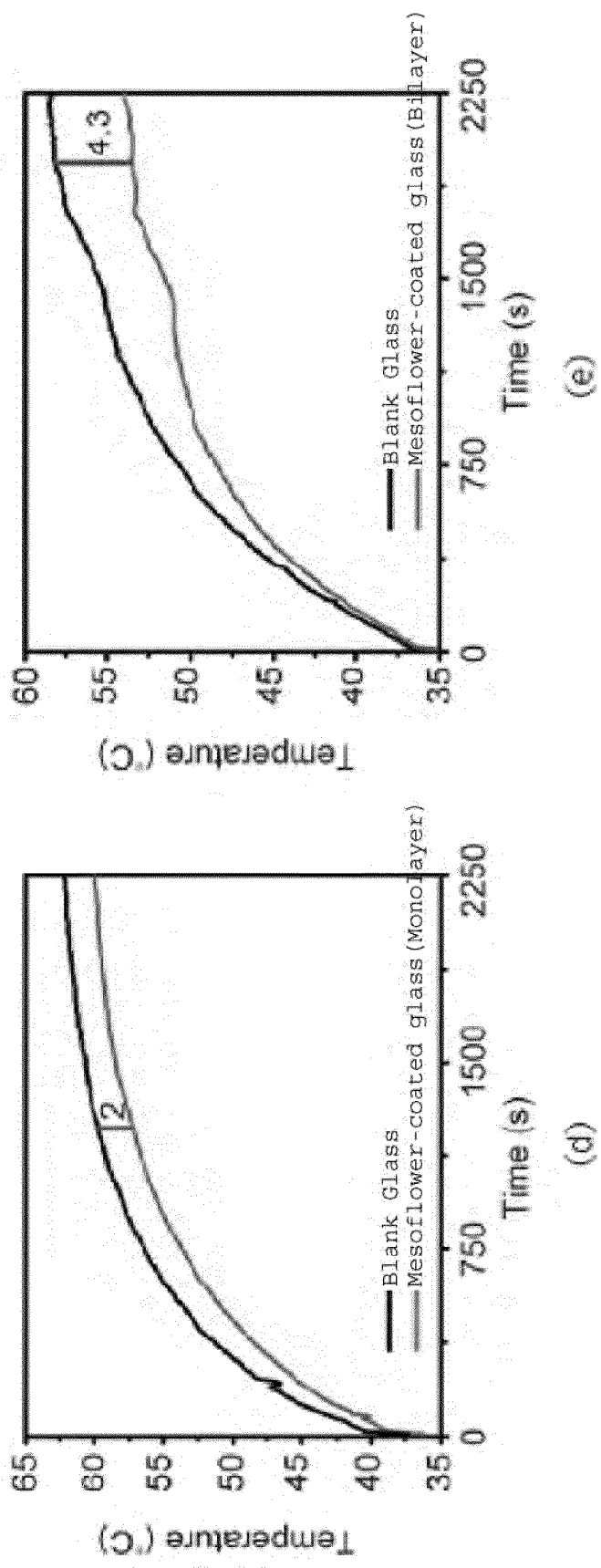

Mesoflowers were coated onto a glass substrate (3 cm×3 cm×0.2 cm) and the absorption spectrum was measured in the UV-vis-NIR region (in the same way as for the solution phase measurement). The mesoflower-coated glass substrate showed a noticeable red shift in its absorption maximum as the particle size increased. This was evident from the UV-vis-NIR spectra of monolayer-coated glass plates (FIG. 7(a)). Mesoflowers of size ~0.5 μm showed a broad absorption maximum around 1400 nm whereas the absorption of ~1.5 μm mesoflowers extended beyond 2500 nm. FIG. 7(b) shows the transmittance spectra of the mesoflower-coated glass substrate that we used for the IR absorption study. Even after two layers of coating, the bilayer of mesoflower-coated glass substrate showed around 80% transmittance in the visible region (FIG. 7(b)). Such high transparency in the visible region together with significant NIR absorption makes them promising candidates for developing IR absorbing materials and thin films.

FIG. 7(c) shows a photograph of the apparatus used for the real-time measurements of NIR-IR absorption properties of gold mesoflowers. The experimental set-up consists of square cardboard boxes with exposed top and bottom sides. The glass substrate of dimensions 15 cm×15 cm with a thickness of 5 mm was placed at the top of a cardboard box in such a way that the sunlight falls perpendicular to the plane of the glass plate. The experiment was carried out with both blank and mesoflower-coated glass substrates simultaneously. The temperature inside the cardboard boxes was measured using copper-constantan thermocouples. The measurements were done during a peak summer day at Chennai (longitude: 80° 4'31" E, latitude: 13°00'19" N) at 1:00 p.m. (IST) where the intensity of sunlight was a maximum. The outside temperature was around 42° C. (the increase in temperature inside the enclosure compared to the outside during the measurements is largely due to the greenhouse effect). The data were collected every ten seconds and the experiments were carried out until the temperature inside the box became constant. Separate experiments with a monolayer and a bilayer of mesoflower-coated glass slides were done along with a blank glass substrate as the control. Compared with the blank glass substrate, the mesoflower monolayer-coated glass gave an average temperature inside the cardboard box which was lower by 2° C., whereas the bilayer-coated substrate showed a reduction of 4.3° C.

FIGS. 7(d) and 7(e) show the plots of variation of temperature inside the cardboard boxes as a function of exposure time for the monolayer and bilayer covered glass plate, respectively. The significant reduction in the temperature exhibited by the mesoflower-coated glass should be useful in the development of cost-effective NIR-IR absorbing coatings for windows. A control experiment was done by using two blank glass plates of the same kind in the two cardboard boxes, which resulted in almost identical temperatures inside both throughout the measurements.

Figure 8:
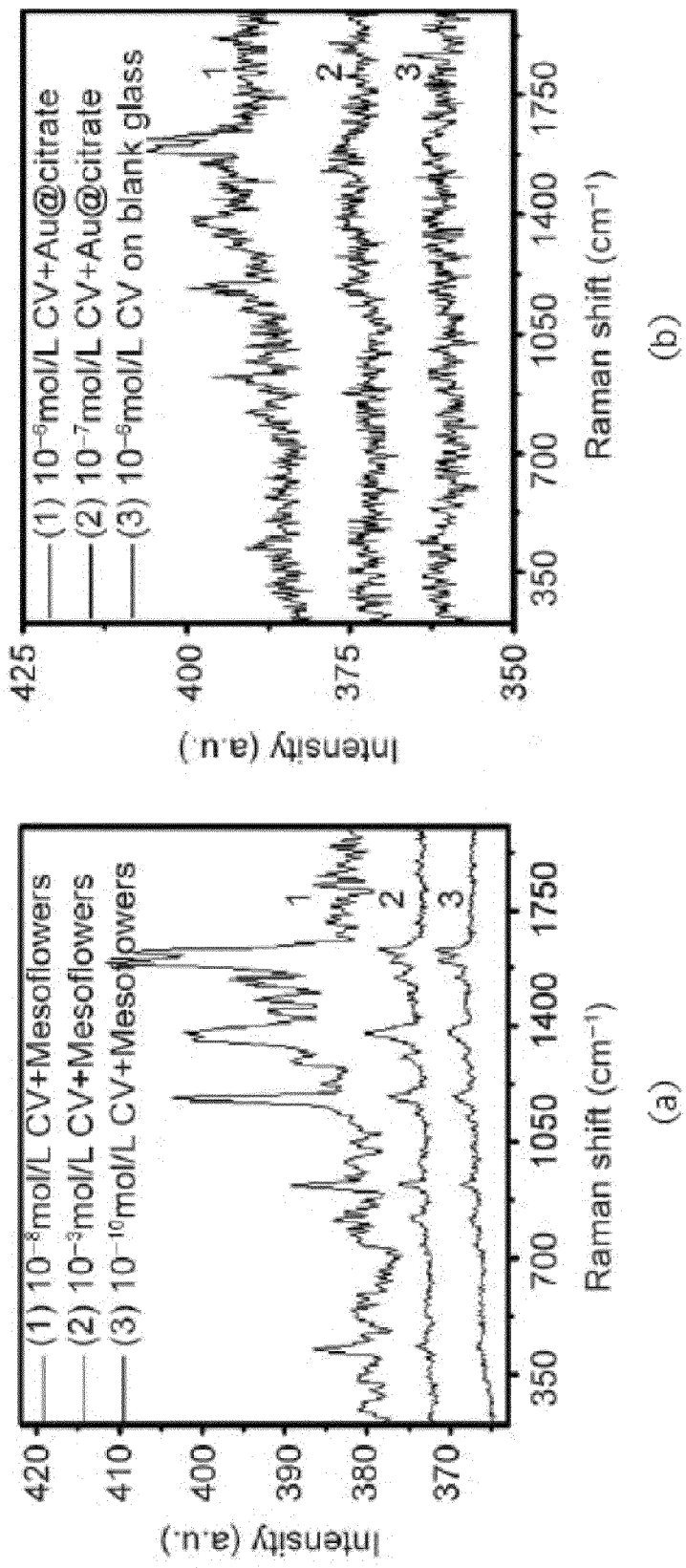
FIG. 8 shows Raman spectra collected from CV solutions of different concentrations adsorbed on (a) mesoflower-coated glass substrate and (b) Au@citrate (spherical NPs)-coated glass substrate; (c) Raman image of a single mesoflower obtained by integrating Raman intensities of $10^{-6}$ mol/L CV solution in the 200-1800 $cm^{-1}$ window; (d) single Raman spectra from various points marked in (c). The inset in (c) is an optical image of the mesoflower.
Figure 8:
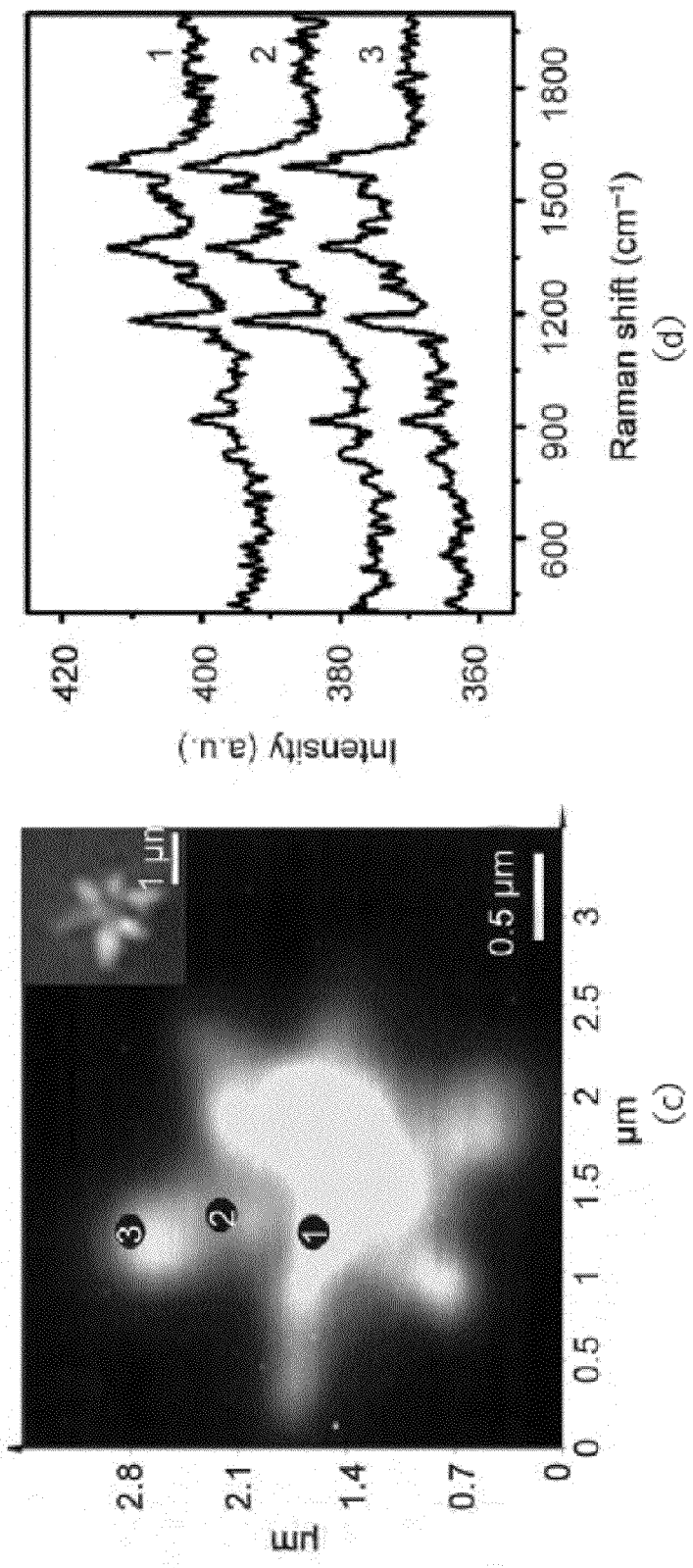

The SERS activity of a monolayer of mesoflowers using crystal violet (CV) as the analyte molecule was measured and collected. The Raman spectra of CV adsorbed on the mesoflowers at different concentrations is shown in FIG. 8(a). The material showed well-defined spectral features of CV even at a concentration of $10^{-10}$ mol/L. In order to compare the SERS activity of the mesoflowers with its spherical analogue, the SERS spectra of CV molecules adsorbed on Au@citrate nanoparticles (NPs) was collected. FIG. 8(b) shows the SERS spectra collected from CV adsorbed on NPs (traces 1 and 2) and from a blank glass plate (trace 3). The NP-coated substrate showed SERS signals down to a CV concentration of $10^{-6}$ mol/L. At a concentration of $10^{-7}$ mol/L, no distinct Raman signals were observed. In the case of $10^{-6}$ mol/L of CV spotted on a blank glass plate, no Raman features were observed. The SERS enhancement factor was calculated for the mesoflowers and it was found to be ~$10^9$ for the 1593 cm$^{-1}$ feature. The corresponding value for the NPs was of the order of $10^4$. The high SERS activity of the mesoflowers may be due to the large electric field enhancement at the sharp tips of each mesoflower as well as the "hot spots" created in between the mesoflowers by the interlocking of two or more mesoflowers. The results indicate that these materials should be useful for making SERS-based sensors. It was found that a single mesoflower particle can be observed using the Raman signals of adsorbed CV at a concentration of $10^{-6}$ mol/L. By collecting the SERS signals, ranging from 200 to 1800 cm$^{-1}$, a single mesoflower was imaged (FIG. 8(c)). The corresponding optical image of the mesoflower is shown in the inset. The Raman spectra collected from the different areas of the mesoflower are shown in FIG. 8(d). It is clear from the intensities of the Raman features that the enhancement is almost the same for different areas over the mesoflower.

Figure 9:
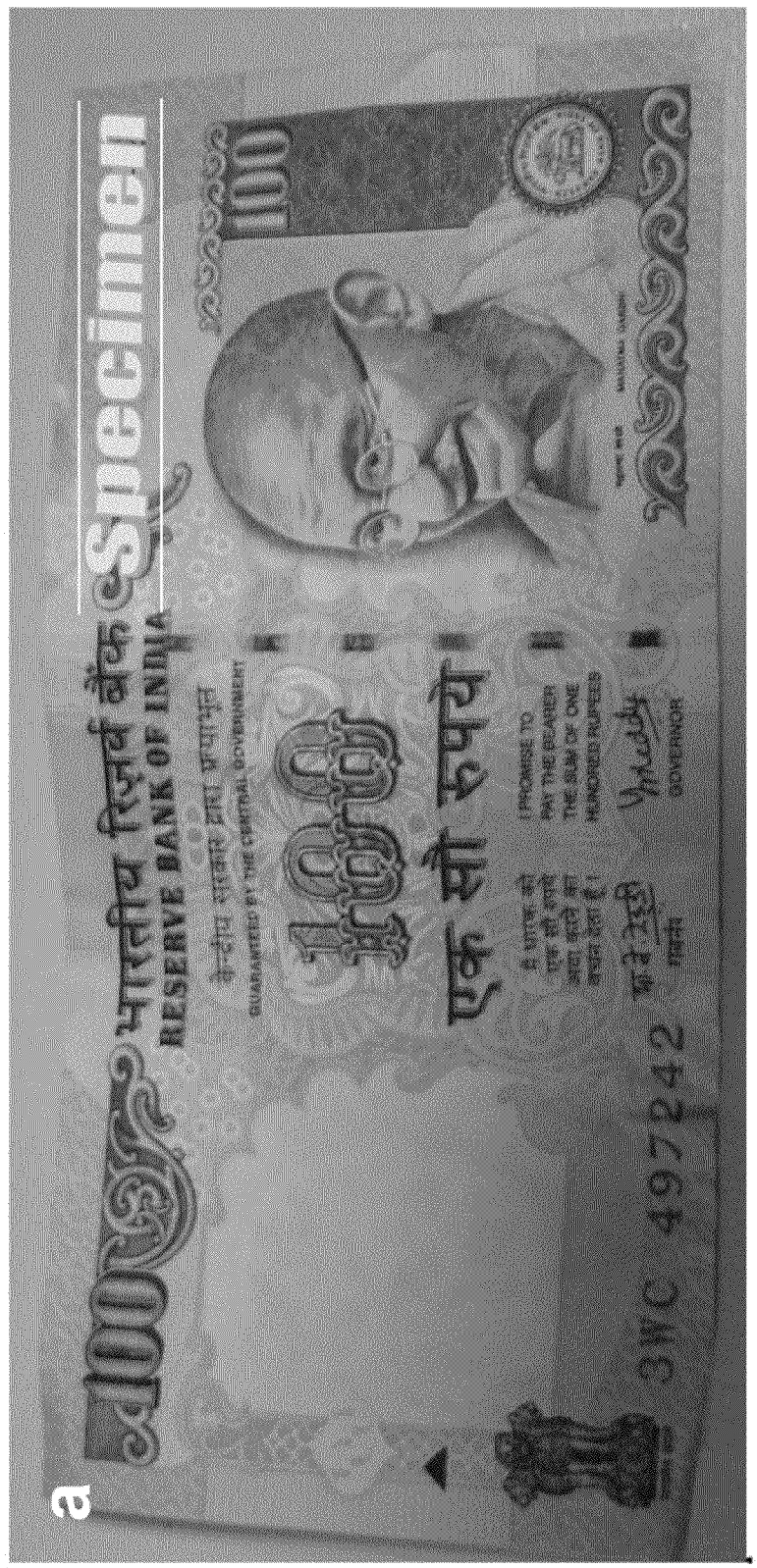
FIG. 9(a) shows a photograph of the mesoflower-embedded Indian currency. (b) A Raman image of the mesoflower on the paper currency. Raman image was collected by integrating intensities of the Raman features in the 200 to 1800 $cm^{-1}$ region. Inset 'b' shows corresponding optical images of the mesoflowers selected for Raman imaging. (c) Raman spectrum collected from a single mesoflower on the paper currency. Currency shown here is for the purpose of illustration.
Figure 9:
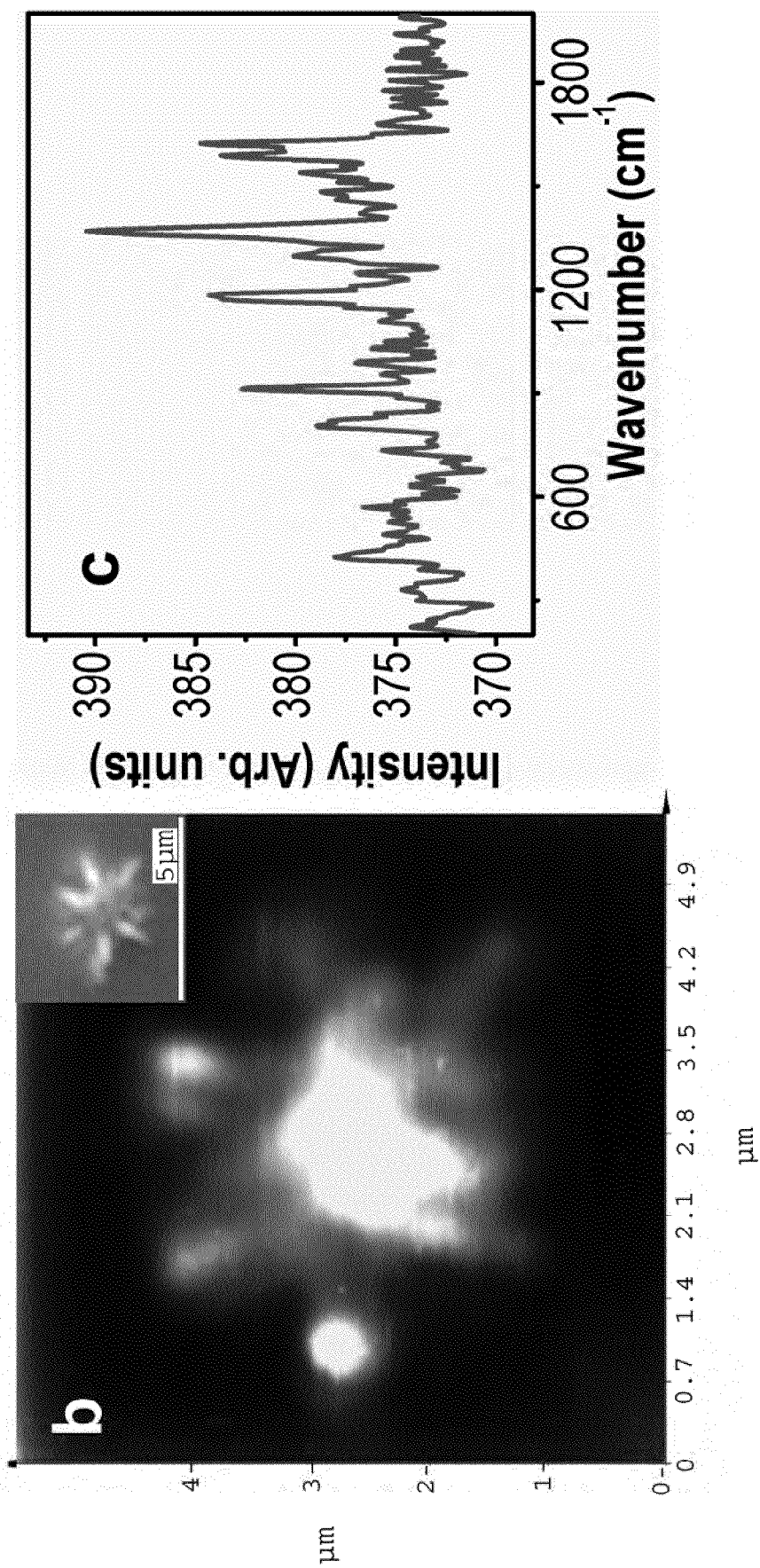

The use of mesoflowers as a security marker was demonstrated by incorporating them onto an Indian currency. A molecular tag such as crystal violet was attached to the mesoflower by soaking of 0.1 mg of mesoflower in 10 mL of $10^{-6}$ M of CV in water for 1 h. The mesoflower suspension so prepared was drop-casted on a specific region of the paper currency. FIG. 9(a) shows the photograph of the mesoflower-embedded on an Indian currency. The portion of the currency where the CV tagged mesoflowers were applied was washed under running water for 1 min. The presence of the mesoflowers and spectroscopic features after repeated water washing, subsequent drying, mechanical rubbing and blowing of air were ascertained. Thus the mesoflowers are retained on the surface even after scratching and washing. A Raman image was collected by integrating intensities of the Raman features in the 200 to 1800 cm$^{-1}$ region (FIG. 9(b)). Inset 'b' shows corresponding optical images of the mesoflowers selected for Raman imaging. Raman spectrum collected from a single mesoflower on a paper currency is shown in FIG. 9(c).

The mesoflowers could be biomimetic structures, resembling several naturally occurring objects such as star fish, aloe vera, pineapple, etc. Each mesoflower was made of a large number of spiky stems, which are projecting outwards from the core, in all directions. The stems were bearing high resemblance to a hierarchical array of scales or plate-like subunits having nano dimensions which themselves have the shape of stars, forming a pyramid of stars. The thickness of such plates and gap between each scale-like subunit were also in nanoscale dimension. These stems show an unusual pentagonal symmetry and maintain an angle of ~72 degrees in between each successive lobe of the stars. Each stems of mesoflowers possess simple and remarkably well-defined uniform stars with 5 vertices. From a detailed investigation of a single stem, it was found that each stem has ridges along its corners. These ridges had nanometer thickness. These ridges gave unique morphology to the stem. The diameter of the sharp, spherical tip of the stems was in the range of 5-10 nm. The features are inherent features of the mesoflower. These features were unique that cannot be replicated. Apart from the above mentioned inherent and unique structural features, the features could have additional attributes in the form of Raman or fluorescent tags and multiple elemental constituents. These features could further improve the level of the security at different authentication stages. Incorporation of molecular tags can be done by simple adsorption technique. It is also possible to attach molecular tags via chemical bonds. The presence of such a tag molecule would not affect the structural attributes of the mesoflower. The unique spectral features of the adsorbed Raman or fluorescent molecules enable the mesoflower to provide exceptional security. These mesoflowers yield bimetallic mesoflowers on treatment with Pt or Ag salt in presence of ascorbic acid. It is possible to incorporate magnetic attributes on the mesoflowers by the overgrowth of various paramagnetic metals such as Fe, Ni, Co, etc. in presence of suitable reducing agents. For that, reducing agents such as hydrazine hydrate, sodium borohydride, etc. can be used. Thus, core-shell kind of magnetic mesoflowers could be made. Because of the presence of the magnetic shell, the mesoflower could show magnetic property. It would be possible to maintain the structural attributes, same as the parent mesoflower, in the bimetallic mesoflowers. Composition of such multi-metallic mesostructures can also be tuned by adjusting the experimental parameters. Suitable instruments for detection of the mesoflowers include: 1) Hand held microscope or optical microscope. 2) UV lamp. 3) Raman and fluorescence spectrometer. 4) Scanning and transmission electron microscopes. 5) Energy dispersive X-ray analyzer. 6) Magnetometer. Depending on the convenience and security, molecular tags can be added to the mesoflower, thereby varying the chemical composition of the mesoflower. Any of such materials can be used for the multilevel security purpose.

Examples are, Raman or fluorescent tags adsorbed gold mesoflower, bimetallic mesoflowers such as Au/Ag, Au/Pt, Au/Pd, Au/Fe, etc., trimetallic mesoflowers like (Au/Pt/Ni, Au/Pt/Fe, etc.), etc.

In the detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A man-made object comprising:
   at least one mesoflower having a distinctive structure with a feature to identify the object,
   wherein the at least one mesoflower has a size such that the at least one mesoflower is observable under visible light,
   wherein a size of the feature is such that the feature is not observable under visible light,
   wherein the feature comprises an attribute originating from the feature, and
   wherein the attribute defines the feature.

2. The object of claim 1, wherein a longest dimension of the object is in a range of 0.1 µm to 10 µm and the size of the feature is about 100 nm or less.

3. The object of claim 1, wherein the feature comprises a plurality of unique elements, each unique element in the plurality of unique elements having a distinct pattern.

4. The object of claim 1, wherein the feature comprises a plurality of unique elements, each unique element in the plurality of unique elements having a distinct property.

5. The object of claim 1, wherein the feature comprises a tag, the tag being associated with the object such that the identification of the tag allows authentication of the object.

6. The object of claim 5, wherein the tag is selected from the group consisting of a molecular tag, a biological tag, an optical tag, an electronic tag, a magnetic tag, a fluorescent tag, a Raman spectroscopy tag, an electron microscopy tag, an X-ray microcopy tag, and combinations thereof.

7. The object of claim 1, wherein the feature is not observable without a specialized device configured to detect the feature.

8. The object of claim 7, wherein the specialized device is configured to detect optical, Raman, fluorescence, electron, X-ray or magnetic properties of the feature.

9. The object of claim 1, wherein the feature comprises a unique element at a level of at least one of a molecule, an atom, and a single particle.

10. The object of claim 1, wherein the feature comprises a plurality of unique elements, wherein each unique element in the plurality of unique elements is configured to be detected at a different stage of authentication of the object.

11. A system comprising multiple diagnostic devices configured to authenticate an object comprising at least one mesoflower, the at least one mesoflower having a feature to identify the object, wherein the feature comprises a plurality of unique elements, each unique element in the plurality of unique elements having a distinct pattern and a distinct property.

12. The system of claim 11, wherein the multiple diagnostic devices comprise at least one of an optical diagnostic device, a Raman diagnostic device, an electron diagnostic device, an X-ray diagnostic device, and a magnetic diagnostic device.

13. The system of claim 11, wherein the feature has specific structural attributes.

14. The system of claim 11, wherein the feature comprises a tag, the tag being associated with the object such that the identification of the tag allows authentication of the object.

15. The system of claim 11, wherein a longest dimension of the object is in a range of 0.1 μm to 10 μm and a size of the feature is about 100 nm or less.

16. A method of authenticating an object comprising at least one mesoflower, the method comprising:
 characterizing a feature of the at least one mesoflower; and
 authenticating the object based on a result of the characterizing the feature,
 wherein the feature comprises a plurality of unique elements configured to be detected during characterization of the object.

17. The method of claim 16, wherein the characterization is done by a system comprising multiple diagnostic devices.

18. The method of claim 17, wherein the multiple diagnostic devices comprise at least one of a optical diagnostic device, a Raman diagnostic device, an electron diagnostic device, an X-ray diagnostic device, and a magnetic diagnostic device.

19. The method of claim 16, wherein the feature comprises a plurality of unique elements, each unique element in the plurality of elements having a distinct pattern and a distinct property.

20. The method of claim 16, wherein a longest dimension of the object is in a range of 0.1 μm to 10 μm and a size of the feature is about 100 nm or less.

21. A near-infrared-infrared (NIR-IR) absorbing coating comprising:
 a mesoflower,
 wherein the NIR-IR absorbing coating absorbs infrared radiation to cause a reduction in a temperature of a first enclosure encased with the NIR-IR absorbing coating versus a temperature of a second enclosure that is not encased with the NIR-IR absorbing coating,
 wherein the first and second enclosures are of substantially same shape and dimensions, and the first and second enclosures are exposed to substantially same environments.

* * * * *

UNITED STATES PATENT AND TRADEMARK OFFICE
CERTIFICATE OF CORRECTION

PATENT NO. : 8,659,391 B2
APPLICATION NO. : 12/636370
DATED : February 25, 2014
INVENTOR(S) : Pradeep et al.

Page 1 of 1

It is certified that error appears in the above-identified patent and that said Letters Patent is hereby corrected as shown below:

On the Title Page, in Item (56), under "OTHER PUBLICATIONS", in Column 2, Line 3, delete "et a1.," and insert -- et al., --, therefor.

In the Specification

In Column 3, Line 24, delete "days. (d)" and insert -- days; (d) --, therefor.

In Column 8, Line 24, delete "of 80 0 C" and insert -- of 80° C. --, therefor.

In Column 9, Line 36, delete "FIG. 4(c) (f)" and insert -- FIGS. 4(c)-(f) --, therefor.

In Column 10, Line 41, delete "Au, Aug," and insert -- Au, $Au_2$, --, therefor.

Signed and Sealed this
First Day of July, 2014

Michelle K. Lee
*Deputy Director of the United States Patent and Trademark Office*